(12) United States Patent
Boismier

(10) Patent No.: US 7,163,550 B2
(45) Date of Patent: Jan. 16, 2007

(54) METHOD FOR MANUFACTURING MEDICAL DEVICES FROM LINEAR ELASTIC MATERIALS WHILE MAINTAINING LINEAR ELASTIC PROPERTIES

(75) Inventor: Dennis A. Boismier, Shorewood, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 708 days.

(21) Appl. No.: 10/400,014

(22) Filed: Mar. 26, 2003

(65) Prior Publication Data

US 2004/0193207 A1   Sep. 30, 2004

(51) Int. Cl.
*A61M 29/00*   (2006.01)

(52) U.S. Cl. .................................. 606/200
(58) Field of Classification Search .............. 606/200, 606/113, 114, 127, 159; 128/898
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,842,579 A | 6/1989 | Shiber | |
| 4,873,978 A | 10/1989 | Ginsburg | |
| 4,886,061 A | 12/1989 | Fischell et al. | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,057,114 A | 10/1991 | Wittich et al. | |
| 5,067,957 A | 11/1991 | Jervis | |
| 5,069,226 A | 12/1991 | Yamauchi et al. | |
| 5,071,407 A | 12/1991 | Termin et al. | |
| 5,100,423 A | 3/1992 | Fearnot | |
| 5,102,415 A | 4/1992 | Guenther et al. | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—Kevin T. Truong
(74) *Attorney, Agent, or Firm*—Crompton, Seager & Tufte LLC

(57) ABSTRACT

Medical devices and methods of manufacturing medical devices at least partially from linear elastic materials. The manufacturing methods may include cold-forming and/or low-temperature heat setting to construct medical devices.

20 Claims, 2 Drawing Sheets

U.S. PATENT DOCUMENTS

| | | | |
|---|---|---|---|
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,197,978 A | 3/1993 | Hess |
| 5,224,953 A | 7/1993 | Morgentaler |
| 5,230,348 A | 7/1993 | Ishibe et al. |
| 5,238,004 A | 8/1993 | Sahatjian et al. |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,411,476 A | 5/1995 | Abrams et al. |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,597,378 A | 1/1997 | Jervis |
| 5,637,089 A | 6/1997 | Abrams et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,796 A | 6/1998 | Palermo et al. |
| 5,769,816 A | 6/1998 | Barbut et al. |
| 5,776,162 A | 7/1998 | Kleshinski |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,836,969 A | 11/1998 | Kim et al. |
| 5,843,244 A | 12/1998 | Pelton et al. |
| 5,846,247 A | 12/1998 | Unsworth et al. |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,902,317 A | 5/1999 | Kleshinski et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,951,793 A | 9/1999 | Mitose et al. |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| RE36,628 E | 3/2000 | Sagae et al. |
| 6,042,553 A | 3/2000 | Solar et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,096,053 A | 8/2000 | Bates |
| 6,117,154 A | 9/2000 | Barbut et al. |
| 6,117,157 A | 9/2000 | Tekulve |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,571 B1 | 1/2001 | Solar et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,217,589 B1 | 4/2001 | McAlister |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,273,900 B1 | 8/2001 | Nott et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,280,539 B1 | 8/2001 | Abrams et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,346,116 B1 | 2/2002 | Brooks et al. |
| 6,375,670 B1 | 4/2002 | Greenhalgh |
| 6,402,761 B1 | 6/2002 | McAlister |
| 6,428,559 B1 | 8/2002 | Johnson |
| 6,461,370 B1 | 10/2002 | Gray et al. |
| 6,461,453 B1 | 10/2002 | Abrams et al. |
| 6,482,222 B1 | 11/2002 | Bruckheimer et al. |
| 6,485,507 B1 | 11/2002 | Walak et al. |
| 6,511,496 B1 | 1/2003 | Huter et al. |
| 6,517,559 B1 | 2/2003 | O'Connell |
| 6,520,987 B1 | 2/2003 | Plante |
| 6,726,703 B1 * | 4/2004 | Broome et al. ............ 606/200 |
| 6,939,362 B1 * | 9/2005 | Boyle et al. ............... 606/200 |
| 2002/0193824 A1 | 12/2002 | Boylan et al. |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |

| | | |
|---|---|---|
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 812 928 A1 | 12/1997 |
| EP | 0 852 132 A1 | 7/1998 |
| EP | 0 873 734 A2 | 10/1998 |
| EP | 1 127 556 A2 | 8/2001 |
| EP | 1 142 604 A1 | 10/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 02/094111 A2 | 11/2002 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac Surgery," Surgery, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoaqulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy...," American Heart Journal, 129(3):430-435 (1995).

Wholey, Mark H. et al., PTA and Stents in the Treatment of Extracranial Circulation, *The Journal of Invasive Cardiology*, 8(E);25E-30E (1996).

\* cited by examiner

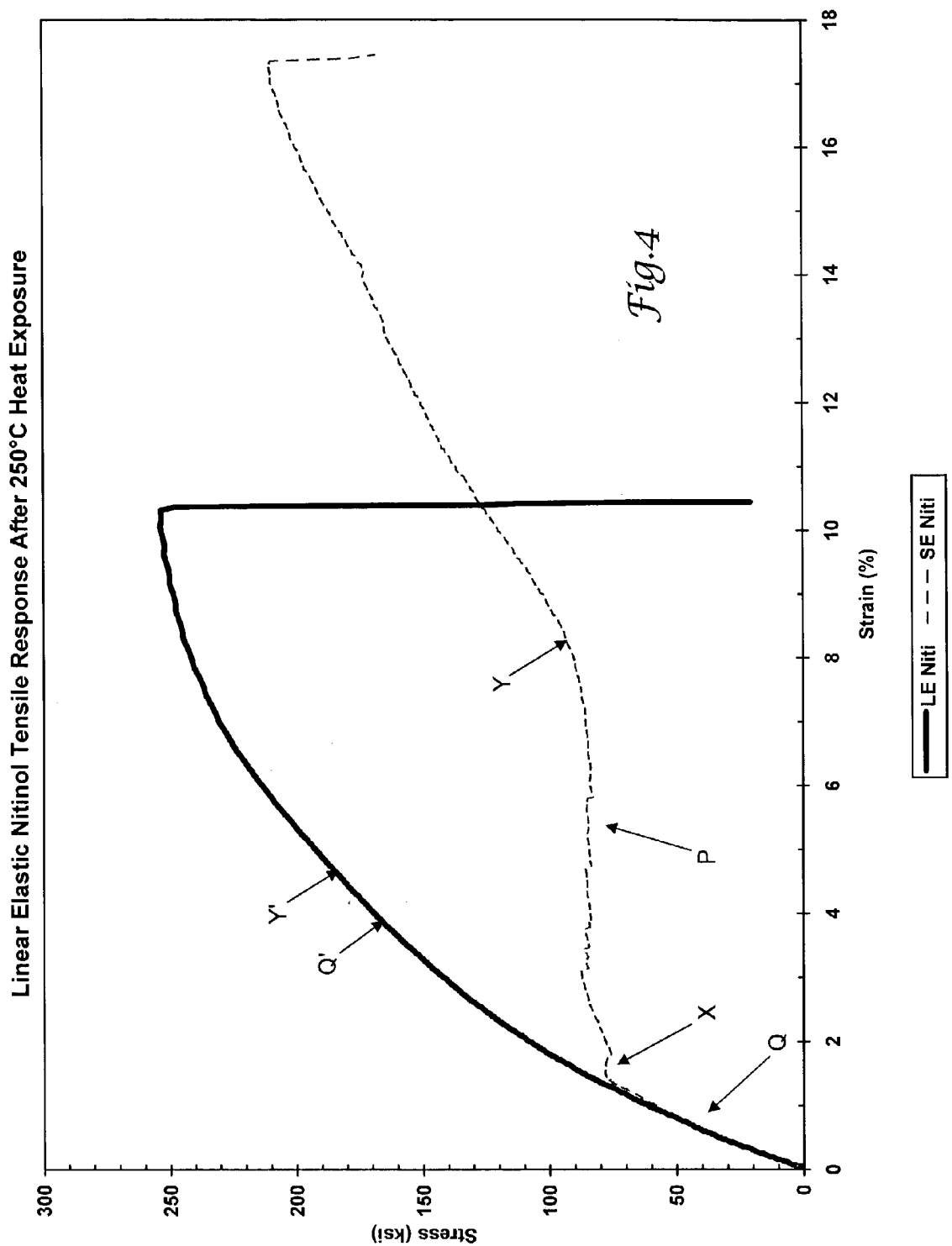

METHOD FOR MANUFACTURING MEDICAL DEVICES FROM LINEAR ELASTIC MATERIALS WHILE MAINTAINING LINEAR ELASTIC PROPERTIES

FIELD OF THE INVENTION

The present invention pertains to medical devices and methods for manufacturing medical devices. More particularly, the present invention pertains to manufacturing medical devices at least in part from linear elastic materials.

BACKGROUND

A vast number of medical devices are available for the treatment of numerous ailments. Each of the different types of devices have certain uses, characteristics, and features. Often the features of a particular device can be derived from the materials used to manufacture the device. For example, a manufacturer may choose to construct a catheter at least partially from flexible materials so that the catheter can bend when navigating the vasculature. The type of flexible material used for making this flexible catheter may further vary depending on the amount of flexibility desired and the practicability of working with the material. Because of the variability among materials, each particular material may have certain advantages and disadvantages. There is an ongoing need for further improvements and refinements to medical devices including improvements regarding the selection of materials and methods used for manufacturing them.

BRIEF SUMMARY

The present invention pertains to medical devices that are at least partially manufactured from linear elastic materials. Additionally, the present invention also pertains to methods for manufacturing medical devices from linear elastic materials. These methods may include, for example, cold-forming and/or low-temperature heat setting. Some examples of these medical devices and methods of manufacturing medical devices are described in more detail below.

BRIEF DESCRIPTION OF THE DRAWINGS

FIG. 4 is a stress-strain curve for linear elastic nitinol after low-temperature heat treatment.

DETAILED DESCRIPTION

Figure 1:
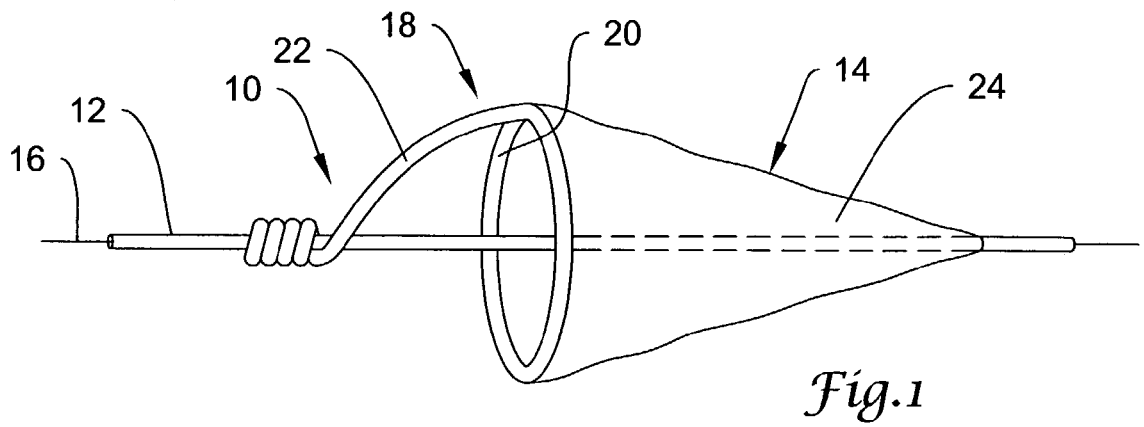
FIG. 1 is a side view of an example medical device.

The following description should be read with reference to the drawings wherein like reference numerals indicate like elements throughout the several views. The detailed description and drawings illustrate example embodiments of the claimed invention.

Shape-memory and super elastic materials, including nickel-titanium alloys such as nitinol, have numerous applications throughout the medical device and other industries. The numerous applications may be due to the shape-memory and super elastic properties of these materials, which may be desirable. The desirable properties of super elastic and shape-memory materials are generally not native to the commercially available or "bulk" materials and, instead, need to be imparted by subjecting them to a number of processing steps. For example, the processing steps may include heat treatment, cold working, and/or other processing steps. In some instances, these processing steps may be sophisticated or complicated.

Some varieties of super elastic materials, for example nitinol alloys, may be commercially available or otherwise can be processed to be "linear elastic". The linear elastic versions of nitinol are similar in chemistry to conventional shape memory and super elastic varieties and may exhibit distinct and useful mechanical properties. For example, linear elastic nitinol does not display a "super elastic plateau" or "flag region" in its stress/strain curve, which are indicative of super elastic nitinol. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range. For example, there may be no martensite/austenite phase changes detectable by DSC and DMTA analysis in the range of about $-150°$ C. to about $400°$ C.

In addition to linear elastic nitinol, a number of other linear elastic or "super elastic precursor" materials are also known and may be available. Some examples of these materials include silver-cadmium alloy, gold-cadmium alloy, gold-copper-zinc alloy, copper-zinc alloy, copper-zinc-aluminum alloy, copper-zinc-tin alloy, iron-beryllium alloy, iron-platinum alloy, indium-thallium alloy, iron-manganese alloy, nickel-titanium-vanadium alloy, iron-nickel-titanium-cobalt alloy, copper-tin alloy, nickel-chromium alloy, nickel-chromium-iron alloy, cobalt alloy, or the like, or other suitable material.

FIG. 1 illustrates an example embolic protection filtering device 10 that is at least partially manufactured from linear elastic or super elastic precursor materials, including any of those listed above. Device 10 may include a shaft 12 and a filter 14 coupled to shaft 12. In some embodiments, shaft 12 may be a guidewire. In other embodiments, shaft 12 may be a tubular filter cartridge configured to be slidable over another device, for example, a guidewire 16. Filter 14 may include a frame assembly 18, which may include a filter loop 20 and one or more struts 22 extending between filter loop 20 and shaft 12. A filter membrane 24 may be coupled to filter loop 20 and, for example, extend distally therefrom. Filter membrane 24 can be drilled (for example, formed by known laser techniques) or otherwise manufactured to include a number of holes or openings. The holes or openings can be sized to allow blood flow therethrough but restrict flow of debris or emboli floating in the body lumen or cavity.

In general, filter 14 may be adapted to operate between a first generally collapsed configuration and a second generally expanded configuration for collecting debris in a body lumen. In some embodiments, filter 14 can be delivered to an appropriate intravascular location, for example "downstream" of an intravascular lesion, using an appropriate filter delivery device. Similarly, filter 14 can be removed from the vasculature at the desired time by an appropriate filter retrieval device.

In at least some embodiments, frame assembly 18 may be at least partially manufactured from linear elastic materials. For example, the portion of frame assembly 18 defining filter loop 20 may be manufactured from linear elastic materials. However, any portion or all of frame assembly 18 may include a linear elastic material. Additionally, other portions of device 10 including shaft 12 may include linear elastic materials. In some embodiments, the linear elastic material may be a nickel-titanium alloy such as linear elastic nitinol. One example of a suitable linear elastic nitinol is FHP-NT alloy commercially available from Furukawa Techno Material Co. of Kanagawa, Japan. It can be appreciated, however, that any of the other materials described herein, or any other appropriate linear elastic or super elastic precursor material may be used.

Figure 2:
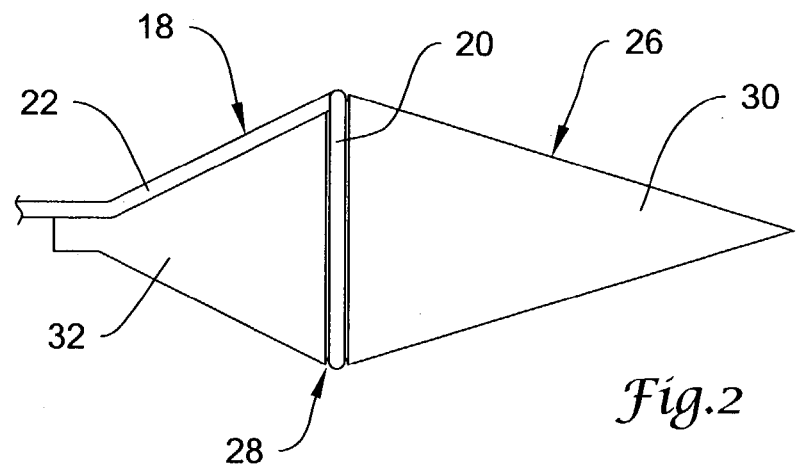
FIG. 2 is a side view of an embolic protection filter frame assembly disposed adjacent a forming member.

The manufacturing of device 10 may generally include disposing the linear elastic material, including those linear elastic materials described herein, about a filter forming member 26 to define frame assembly 18 as shown in FIG. 2. According to this embodiment, forming member 26 may have a shape that is generally configured for manufacturing frame assembly 18. For example, forming member 26 may include a groove or slot 28 (which, for example, may be adapted for defining filter loop 20), a tapered distal region 30, and a proximal region 32. Thus, the linear elastic material can be positioned on forming member 26 such that a portion is disposed in groove 28 to define filter loop 20 and a portion is disposed adjacent proximal section 32 that may define other sections of frame assembly 18 such as the one or more struts 22.

In some embodiments, disposing the linear elastic material on forming member 26 to define frame assembly 18 may include cold-forming or room temperature shape setting. In general, cold-forming is understood to be forming, bending, shaping, or otherwise altering the shape of the linear elastic material to define frame assembly 18 without substantially increasing temperature or changing the thermal conditions. For example, cold-forming may occur at temperatures near the ambient room temperature such as about 15–25 degrees Celsius. Although some materials such as linear elastic nitinol may have a tendency to crack when highly deformed, this was, unexpectedly, not found to be the case.

The cold-formed linear elastic nitinol, after disposing it on forming member 26, somewhat unexpectedly can retain the set shape corresponding to the shape of frame assembly 18. However, a certain amount of "spring-back" may be observed. Spring-back is understood to be the tendency of the cold-formed linear elastic material to partially spring back or enlarge to a size that is slightly larger than the size that would otherwise be defined by shaping member 26. The amount of spring-back may vary depending on the material used, amount of thermal energy added (if any), and other factors. However, the amount of spring-back has been found to be substantially consistent among consistent manufacturing conditions. Thus, a manufacturer can reproducibly predict the expected amount of spring-back for essentially any given set of materials and/or thermal conditions.

Because of spring-back, some example manufacturing methods may include manufacturing frame assembly 18 by disposing a linear elastic material on a forming member 26 that is reduced in size. For example, the reduced size forming member 26 may be about 1.25–3 times smaller (i.e., about ⅓ to ⅘ the size of a forming member that might be used in the absence of spring-back). More particularly, forming member 26 may be sized to define a reduced size or "pre spring-back" frame assembly 18 that is about 1.25–3 times smaller than the desired final size for frame assembly 18. After forming the reduced size frame assembly 18, it can spring-back or enlarge to the desired full or final size frame assembly 18. Moreover, given the reproducibility of spring-back, a manufacturer can vary the size of forming member 26 and the thermal conditions to produce frame assemblies in a wide variety of sizes.

Figure 3:
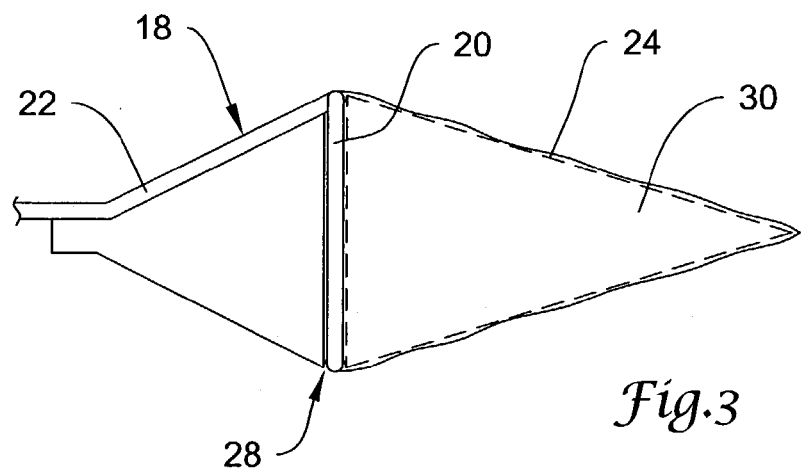
FIG. 3 is a side view of the embolic protection filter frame assembly and forming member shown in FIG. 2 with a filter membrane coupled to the frame assembly.

In some embodiments, the cold-formed frame assembly 18 may be coupled to filter membrane 24 in any appropriate manner (e.g., dip-molding, spray molding, thermal or adhesive bonding, and the like), as shown in FIG. 3. In some embodiments, filter membrane 24 may be disposed over distal region 30 of forming member 26 and coupled to filter loop 20. Frame assembly 18 and filter membrane 24 can be dissociated from forming member 26 and may be further processed. For example, the disassociated frame assembly 18 and filter membrane 24 can be coupled to shaft 12 in essentially any appropriate manner.

In some other embodiments, frame assembly 18 can be manufactured using low-temperature heat setting. According to this embodiment, the linear elastic material can be can be disposed on forming member 26 to define frame assembly 18 (as shown in FIG. 2) and subjected to a relatively low-temperature heat treatment. For example, the heat treatment may include the linear elastic frame assembly 18 at temperatures of about 275° Celsius or less, for example about 150–375° Celsius, or for example about 200–300° Celsius, or for example about 225–275° Celsius, etc. These thermal conditions are lower than those typically used for shape setting super elastic material, which may be about 400–550° Celsius or more. Of course the precise temperature conditions may vary, depending on the material used. The amount of time over which the low-temperature heat setting occurs may also vary. For example, the linear elastic frame assembly 18 may be low-temperature heat set for about 5–60 minutes or more or less.

It is believed that low-temperature heat setting results in the material being substantially set to the desired shape, but results in the material having or maintaining linear elastic properties instead of acquiring super elastic properties. For example, FIG. 4 illustrates an example stress-strain curve for a super elastic nitinol material (SE Niti) and for linear elastic nitinol (LE Niti) that is low-temperature heat set at 250° Celsius. The stress-strain curve of the super elastic nitinol shows that in a first region Q of the curve, as stress is increased the strain also increases in a generally proportional manner. The proportional increases in stress and strain continue to a point X. Beyond point X, the material passes through a plateau region P, which is characteristic of super elastic materials, where the material continues to elongate while stress remains relatively constant. At some point, the super elastic nitinol reaches its yield point Y. The low-temperature heat set linear elastic nitinol also exhibits generally proportional increases in stress and strain through region Q', similar to the super elastic nitinol. However, the stress-strain curve for the linear elastic material does not include a plateau region. Instead, stress and strain continue to increase proportionally to a yield point Y' (beyond which the material plastically deforms) and, eventually, to a fracture or failure point. The yield point Y' for linear elastic nitinol has been found to be at about 4% strain. Thus, linear elastic nitinol could have up to about 4% recoverable strain. Similar observations were made under differing heat setting conditions, including variations in temperature (about 300° Celsius or less) and in the length of time that heat setting occurs over (in the range of about 5–60 minutes).

Although the above discussion describes some the manufacturing methods for constructing filtering devices at least partially from linear elastic materials, this is not intended to be limited to just filtering devices. It can be appreciated that a number of other medical devices may be similarly manufactured from linear elastic materials according the manufacturing methods described herein. For example, some of the other types of medical devices may include electrophysiology baskets, stents, stent connectors, guidewire coils and couplers, vena cava filters, snares, stiffening wires and mandrels for catheters, support coils or ribbons for catheters, bone anchors, orthodontic wires and devices, curved needles and other direct injection drug delivery devices, electrodes, heart valves, distal protection filters and filter baskets, and the like.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of manufacturing an embolic protection filtering device, comprising the steps of:
    providing a linear elastic shaft;
    providing a filter shaping member, the shaping member including a filter loop defining region; and
    disposing the linear elastic shaft adjacent the filter loop defining region, wherein disposing the linear elastic shaft adjacent the filter loop defining region alters the shape of the linear elastic shaft so that it substantially conforms to the shape of the filter loop defining region to define a filter loop, and wherein the filter loop exhibits a linear elastic response to stress.

2. The method of claim 1, wherein the linear elastic shaft includes a linear elastic nickel-titanium alloy.

3. The method of claim 1, wherein the filter shaping member is smaller in size than the filter loop so that the step of disposing the linear elastic shaft adjacent the filter loop defining region includes defining a preliminary filter loop that expands to define the filter loop when the shaft and the mandrel are disassociated.

4. The method of claim 1, wherein the step of disposing the linear elastic shaft adjacent the filter loop defining region occurs at a temperature in the range of about 15 to 25 degrees Celsius.

5. The method of claim 1, wherein the step of disposing the linear elastic shaft adjacent the filter loop defining region includes heat treatment.

6. The method of claim 5, wherein heat treatment includes heating the shaft at a temperature less than 300 degrees Celsius.

7. The method of claim 5, wherein heat treatment includes heating the shaft for about 5 to about 60 minutes.

8. The method of claim 1, further comprising the step of coupling a filter membrane to the filter loop.

9. The method of claim 1, further comprising the step of coupling the filter loop to a shaft member.

10. The method of claim 9, wherein the shaft member is a guidewire.

11. The method of claim 9, wherein the shaft member is a tubular filter cartridge.

12. An embolic protection filtering device, comprising:
    a shaft;
    a filter coupled to the shaft, the filter including a filter frame assembly and a filter membrane coupled to the filter frame assembly and extending distally therefrom, the frame assembly including a filter loop and one or more struts extending between the filter loop and the shaft; and
    wherein at least a portion of the frame assembly includes a linear elastic material.

13. The filtering device of claim 12, wherein the filter loop includes a linear elastic material.

14. The filtering device of claim 12, wherein the linear elastic material includes nickel-titanium alloy.

15. A method of manufacturing an embolic protection filter, comprising the steps of:
    providing a linear elastic shaft formed at least in part from a precursor of a superelastic material;
    forming the linear elastic shaft into a shape that defines a filter loop and one or more struts, the loop and struts having linear elastic properties;
    coupling a filter membrane to the filter loop; and
    coupling the one or more struts to a shaft member.

16. The method of claim 15, wherein the step of forming the linear elastic shaft into a shape that defines a filter loop and one or more struts includes disposing the linear elastic shaft about a forming member.

17. The method of claim 15, wherein the step of forming the linear elastic shaft into a shape that defines a filter loop and one or more struts includes low-temperature heat setting.

18. The method of claim 17, wherein low-temperature heat setting includes heat setting at a temperature less than about 300 degrees Celsius.

19. The method of claim 17, wherein low-temperature heat setting includes heat setting for about 5 to about 60 minutes.

20. A method of manufacturing an embolic protection filtering device, comprising the steps of:
    providing a nickel-titanium alloy shaft;
    disposing the shaft on a forming member;
    heat-treating the shaft at a temperature less than about 300 degrees Celsius so as to define a filter frame assembly, and wherein the frame assembly exhibits linear elastic properties.

* * * * *